(12) United States Patent
Webb

(10) Patent No.: US 9,895,171 B2
(45) Date of Patent: Feb. 20, 2018

(54) MODULAR POLYAXIAL BONE SCREW

(71) Applicant: Scott A. Webb, Clearwater, FL (US)

(72) Inventor: Scott A. Webb, Clearwater, FL (US)

(73) Assignee: Transcendental Spine, LLC, Mars, PA (US)

( * ) Notice: Subject to any disclaimer, the term of this patent is extended or adjusted under 35 U.S.C. 154(b) by 29 days.

(21) Appl. No.: 14/812,160

(22) Filed: Jul. 29, 2015

(65) Prior Publication Data
US 2016/0030090 A1 Feb. 4, 2016

Related U.S. Application Data

(60) Provisional application No. 62/030,289, filed on Jul. 29, 2014.

(51) Int. Cl.
*A61B 17/70* (2006.01)
(52) U.S. Cl.
CPC ...... *A61B 17/7037* (2013.01); *A61B 17/7032* (2013.01); *A61B 17/7034* (2013.01)

(58) Field of Classification Search
CPC ............ A61B 17/7032; A61B 17/7034; A61B 17/7037
See application file for complete search history.

(56) References Cited

U.S. PATENT DOCUMENTS

| 5,728,098 A | * | 3/1998 | Sherman | ............ A61B 17/7032 606/269 |
| 5,733,285 A | * | 3/1998 | Errico | ................ A61B 17/7055 606/278 |
| 2014/0031880 A1 | * | 1/2014 | Biedermann | ...... A61B 17/8605 606/305 |

* cited by examiner

*Primary Examiner* — Ellen C Hammond
(74) *Attorney, Agent, or Firm* — Clements Bernard Walker PLLC; Christopher L. Bernard

(57) ABSTRACT

A modular polyaxial bone screw that incorporates a threaded screw including a head portion and a tulip assembly that selectively "snaps" and locks onto the head portion of the threaded screw in a desired orientation. Thus, the threaded screw may be placed in bone before the tulip assembly is engaged onto the head portion of the threaded screw and a rod is disposed and secured there through using a locking cap, thereby locking the tulip assembly onto the head portion of the threaded screw in the desired orientation.

7 Claims, 4 Drawing Sheets

MODULAR POLYAXIAL BONE SCREW

CROSS-REFERENCE TO RELATED APPLICATION

The present patent application/patent claims the benefit of priority of U.S. Provisional Patent Application No. 62/030,289, filed on Jul. 29, 2014, and entitled "MODULAR POLYAXIAL BONE SCREW," the contents of which are incorporated in full by reference herein.

FIELD OF THE INVENTION

The present invention relates generally to a modular polyaxial bone screw for use in a surgical spinal fixation/stabilization procedure or the like. More specifically, the present invention relates to a modular polyaxial bone screw that incorporates a threaded screw including a head portion and a tulip assembly that selectively "snaps" and locks onto the head portion of the threaded screw in a desired orientation. Thus, the threaded screw may be placed in bone before the tulip assembly is engaged onto the head portion of the threaded screw and a rod is disposed and secured there through using a locking cap, thereby locking the tulip assembly onto the head portion of the threaded screw in the desired orientation.

BACKGROUND OF THE INVENTION

One exemplary type of modular polyaxial bone screw contemplated by the present invention is a modular polyaxial pedicle screw. A pedicle is a dense stem-like bony structure that projects from the posterior of a vertebra. There are two pedicles per vertebra that connect to other structures, such as the lamina and the vertebral arch. As the result of various spinal diseases and injuries, a spinal surgeon may choose perform an interbody fusion or the like to fuse adjacent vertebrae using a bone graft and/or an implantable device, or otherwise immobilize a portion of the spine of a patient. Typically, in the interbody fusion case, the adjacent vertebrae are immobilized while the bone graft is allowed to "take," for example, using a conventional pedicle screw system, a plate system, and/or the like.

A pedicle screw is a particular type of bone screw that is designed for implantation into a vertebral pedicle. Pedicle screws can be used in a surgical spinal fusion to add extra support and strength to the fusion while it heals. Pedicle screws are placed above and below the vertebrae that are fused. A rod is used to connect the pedicle screws, which prevents movement and allows the bone graft to heal. After the fusion is completely healed, the pedicle screws and rods can be removed.

Accordingly, surgical spinal procedures often require securing various implants to vertebrae of the spine. The pedicle screw is one such implant and is often used with other components, such as rods, that are then secured to individual pedicle screw implants in order to provide a support or fixation function between and among neighboring vertebrae. Both the rods and pedicle screws may have varying diameters and dimensions depending on patient and therapeutic needs. Due to the complex curvature and anatomy of the spine, it is sometimes difficult to align the pedicle screw and rod holder assembly with the rod, particularly when spanning multiple segments.

Traditionally, this alignment has required extensive bending and test fitting of rods to correctly approximate the rod holding portion of the pedicle screw(s). More recently, a polyaxial screw type has become widely available, which allows the rod receiving portion of the screw to pivot about the screw head. The pivoting head allows the rod holder to interface with the rod with only minimal rod contouring. These polyaxial screws are now the most common type of pedicle screw.

Current pedicle screw designs generally include: 1) a threaded bone screw shaft that is anchored into the pedicle bone of the vertebrae; 2) a rod holding member (i.e. a saddle or tulip assembly) that is attached to the head of the bone screw to receive a rod for stabilization of the spine; and 3) a set screw that interfaces with the top of the rod holder to compress the rod into the holder to form a stable construct.

These components are assembled into two primary design types: monoaxial and polyaxial screw systems. The monoaxial screws typically have a fixed angular relationship between the bone screw and rod holder (i.e. the saddle or tulip assembly). These screw designs dictate that the rod is held perpendicular to the direction of the bone screw. While these designs are strong and stable, they make it difficult to position the screw and rod properly and require a lot of rod bending to correctly approximate the rod holder and rod.

Polyaxial designs allow the rod holding member to pivot on the bone screw head, such that the rod holder can properly interface with a rod that is not perfectly perpendicular to the direction in which the bone screw is inserted. After the set screw is used to compress the rod into the rod holder, the polyaxial design locks into place and no longer allows the rod holder to pivot on the screw head.

Current designs, however, suffer from a limitation in their functionality in that the threaded screw must typically be placed in bone while the tulip assembly is coupled to the threaded screw. This leads to unnecessary complexity in the tooling and placement technique used, thereby sacrificing time and, in some cases, surgical accuracy. Thus, what is still needed in the art is a modular polyaxial bone screw that allows the threaded screw to be placed in bone separately, before the tulip assembly is engaged onto the head portion of the threaded screw.

BRIEF SUMMARY OF THE INVENTION

In various exemplary embodiments, the present invention provides a modular polyaxial bone screw that incorporates a threaded screw including a head portion and a tulip assembly that selectively "snaps" and locks onto the head portion of the threaded screw in a desired orientation. Thus, the threaded screw may be placed in bone before the tulip assembly is engaged onto the head portion of the threaded screw and a rod is disposed and secured there through using a locking cap, thereby locking the tulip assembly onto the head portion of the threaded screw in the desired orientation.

In one exemplary embodiment, the present invention provides a modular polyaxial bone screw, comprising: a threaded screw comprising a head portion and a thread portion; and a tulip assembly comprising an upper portion and a lower portion, wherein the upper portion of the tulip assembly is configured to receive and retain a rod and a locking cap, and wherein the lower portion of the tulip assembly is configured to receive and retain the head portion of the threaded screw; wherein the lower portion of the tulip assembly comprises a locking collar disposed concentrically about a plurality of spring members, and wherein, when the locking collar is translated from a first position about the plurality of spring members to a second position about the plurality of spring members, the plurality of spring members transition from an expanded configuration in which the tulip assembly is allowed to pivot with respect to the threaded screw to a compressed configuration in which the tulip assembly is prevented from pivoting with respect to the threaded screw. The head portion of the threaded screw is substantially spherical in shape. The locking cap is externally threaded and is configured to engage threads manufactured into an interior portion of the tulip assembly. The plurality of spring members define a substantially spherical internal space. Optionally, the locking collar is translated from the first position to the second position using a tool. Alternatively, the locking collar is translated from the first position to the second position via deflection of the rod into the locking collar by insertion and rotation of the locking cap into the tulip assembly. The plurality of spring members are disposed concentrically about the head portion of the threaded screw.

In another exemplary embodiment, the present invention provides a method for providing a modular polyaxial bone screw, comprising: providing a threaded screw comprising a head portion and a thread portion; and providing a tulip assembly comprising an upper portion and a lower portion, wherein the upper portion of the tulip assembly is configured to receive and retain a rod and a locking cap, and wherein the lower portion of the tulip assembly is configured to receive and retain the head portion of the threaded screw; wherein the lower portion of the tulip assembly comprises a locking collar disposed concentrically about a plurality of spring members, and wherein, when the locking collar is translated from a first position about the plurality of spring members to a second position about the plurality of spring members, the plurality of spring members transition from an expanded configuration in which the tulip assembly is allowed to pivot with respect to the threaded screw to a compressed configuration in which the tulip assembly is prevented from pivoting with respect to the threaded screw. The head portion of the threaded screw is substantially spherical in shape. The locking cap is externally threaded and is configured to engage threads manufactured into an interior portion of the tulip assembly. The plurality of spring members define a substantially spherical internal space. Optionally, the locking collar is translated from the first position to the second position using a tool. Alternatively, the locking collar is translated from the first position to the second position via deflection of the rod into the locking collar by insertion and rotation of the locking cap into the tulip assembly. The plurality of spring members are disposed concentrically about the head portion of the threaded screw.

BRIEF DESCRIPTION OF THE DRAWINGS

The present invention is illustrated and described herein with reference to the various drawings, in which like reference numbers are used to denote like assembly components/method steps, as appropriate, and in which.

BRIEF DESCRIPTION OF THE INVENTION

Figure 1:
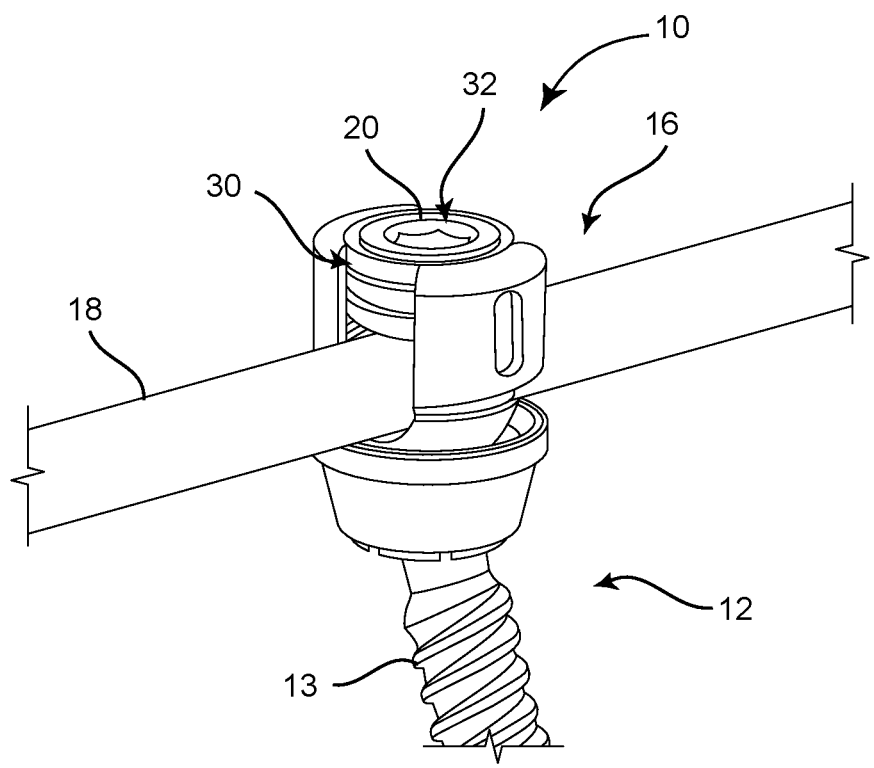
FIG. 1 is a perspective view of one exemplary embodiment of the modular polyaxial bone screw of the present invention, in a fully assembled state with a rod disposed there through and an associated locking cap installed.

Referring to FIGS. 1-4, in various exemplary embodiments, the present invention provides a modular polyaxial bone screw 10 for use in a surgical spinal fixation/stabilization procedure or the like. More specifically, the present invention provides a modular polyaxial bone screw 10 that incorporates a threaded screw 12 including a thread portion 13 and a head portion 14 and a tulip assembly 16 that selectively "snaps" and locks onto the head portion 14 of the threaded screw 12 in a desired orientation. Thus, the threaded screw 12 may be placed in bone before the tulip assembly 16 is engaged onto the head portion 14 of the threaded screw 12 and a rod 18 is disposed and secured there through using a locking cap 20, thereby locking the tulip assembly 16 onto the head portion 14 of the threaded screw 12 in the desired orientation.

Figure 2:
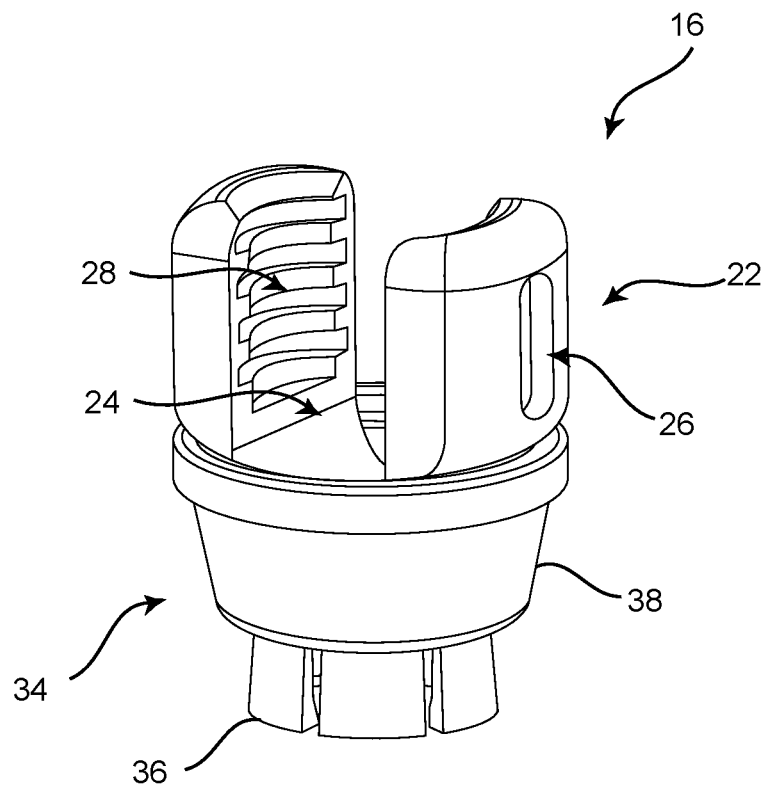
FIG. 2 is a perspective view of one exemplary embodiment of the tulip assembly of the modular polyaxial bone screw of the present invention.
Figure 3:
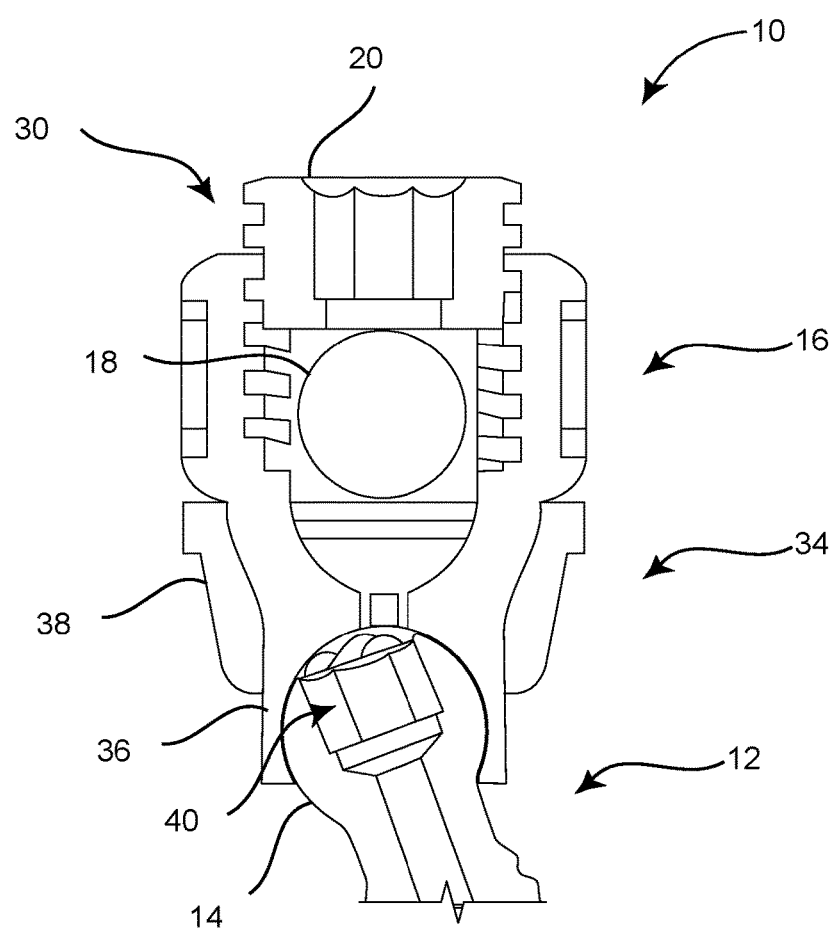
FIG. 3 is a cross-sectional side view of one exemplary embodiment of the modular polyaxial bone screw of the present invention, in a fully assembled state with a rod disposed there through and an associated locking cap partially installed, and with the tulip assembly "unlocked" from the head portion of the threaded screw.
Figure 4:
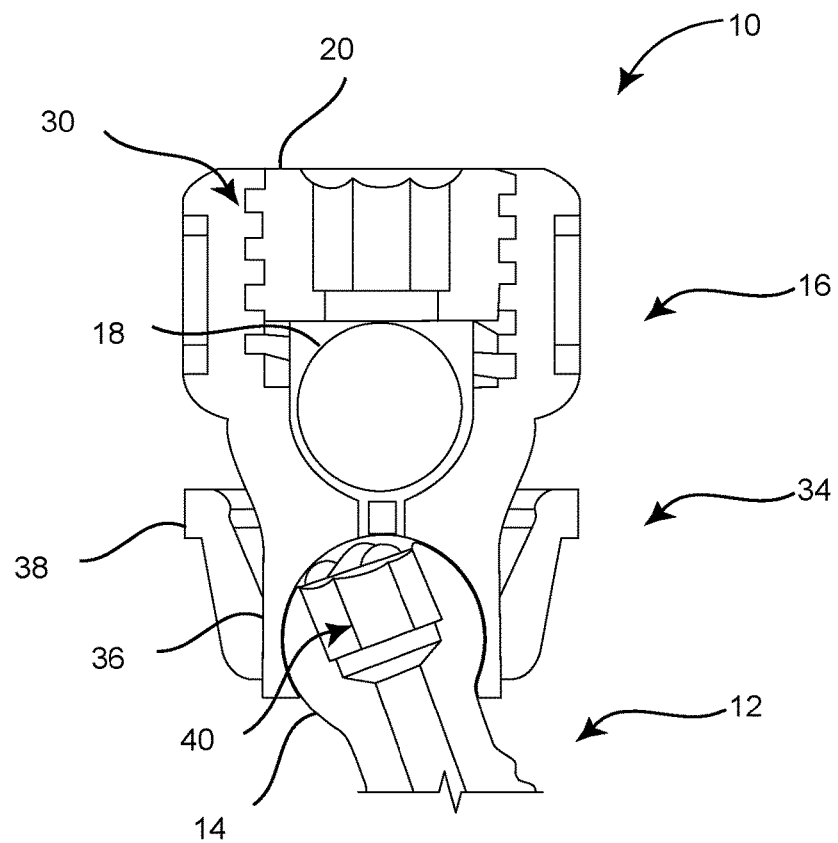
FIG. 4 is another cross-sectional side view of one exemplary embodiment of the modular polyaxial bone screw of the present invention, in a fully assembled state with a rod disposed there through and an associated locking cap fully installed, and with the tulip assembly "locked" to the head portion of the threaded screw.

Referring now specifically to FIG. 2, in one exemplary embodiment, the tulip assembly 16 includes a upper portion 22 that is configured to selectively receive and retain the rod 18 (FIGS. 1, 3, and 4) in a substantially U-shaped channel 24 or the like. The upper portion 22 of the tulip assembly 16 includes one or more tool receiving recesses 26 by which the tulip assembly 16 is selectively grasped and retained by a tool or the like. The upper portion 22 of the tulip assembly 16 also includes internal threads 28 by which the tulip assembly 16 selectively receives and retains the locking cap 20 (FIGS. 1, 3, and 4), which includes external threads 30 (FIGS. 1, 3, and 4). As illustrated in FIG. 1, the locking cap 20 also includes a tool receiving recess 32 that is configured to selectively receive an appropriate driver or the like.

The tulip assembly 16 further includes a lower portion 34 including a plurality of spring fingers 36 or the like and a locking collar 38. In operation, the thread portion 13 (FIG. 1) of the threaded screw 12 (FIGS. 1, 3, and 4) is installed in bone, as desired, and, subsequently, the tulip assembly 16 is "snapped" onto the head portion 14 (FIGS. 1, 3, and 4) of the threaded screw 12, with the plurality of spring fingers 36 or the like being deflected about the head portion 14 of the threaded screw 12 and forming a ball-and-socket type joint there between. For this purpose, the plurality of spring fingers 36 or the like are designed, configured, and positioned to deflect outwards and rebound to a position about the head portion 14 of the threaded screw 12. Accordingly, the head portion 14 of the threaded screw 12 is a substantially spherical structure and includes one or more tool receiving recesses 40 configured to selectively receive a driver or other tool. The plurality of spring fingers 36 collectively define a substantially spherical internal void corresponding to the substantially spherical head portion 14 of the threaded screw 12. The locking collar 38 is disposed concentrically about and retained by the plurality of spring fingers 36, and may be translated to a degree around their length. Using an appropriate tool, the locking collar 38 is deflected from an upper "unlocked" position to a lower "locked" position about the plurality of spring fingers 36, thereby securing the tulip assembly 16 to the head portion 14 of the threaded screw 12. This procedure may be reversed to remove the tulip assembly 16 from the threaded screw 12, and is made possible by the fact that the translation of the locking collar 38 along the length of the spring fingers 36 causes the spring fingers 36 to compress or expand about the head portion 14 of the threaded screw 12. This is due to the fact that the top portion of the spring fingers 36 has a collective diameter that is smaller than the collective diameter of the spring fingers 36 at their bottom portion.

Referring now specifically to FIGS. 3 and 4, when installed, the rod 18 is seated on top of the locking collar 38, and, when an appropriate locking cap 20 is installed in the tulip assembly 16 and tightened, the rod 18 "pushes" the locking collar 38 downwards, thereby "locking" and/or securing the plurality of spring fingers 36 or the like about the head portion 14 of the threaded screw 12. This provides an alternative installation mechanism to the tool procedure described herein above. In effect, the locking collar 38 is secured about the plurality of spring fingers 36 or the like via a cold weld, and one or more detent positions may be provided between the "unlocked" and the "locked" positions of the locking collar 38, thereby providing increasing degrees of resistance between the tulip assembly 16 and the head portion 14 of the threaded screw 12 as the locking collar 38 is deployed downwards about the plurality of spring fingers 36 or the like.

In general, FIG. 3 is a cross-sectional side view of one exemplary embodiment of the modular polyaxial bone screw 10 of the present invention, in a fully assembled state with the rod 18 disposed there through and the associated locking cap 20 partially installed, and with the tulip assembly 16 "unlocked" from the head portion 14 of the threaded screw 12. FIG. 4 is another cross-sectional side view of one exemplary embodiment of the modular polyaxial bone screw 10 of the present invention, in a fully assembled state with the rod 18 disposed there through and the associated locking cap 20 fully installed, and with the tulip assembly 16 "locked" to the head portion 14 of the threaded screw 12.

It will be readily apparent to those of ordinary skill in the art that the modular polyaxial bone screw 10 (FIGS. 1-4) of the present invention may be manufactured from any surgically implantable material and sized as with any conventional polyaxial bone screw. Further, any suitable bone engaging or metal-metal thread patterns may be used, etc.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims.

What is claimed is:

1. A modular polyaxial bone screw, comprising:
a threaded screw comprising a head portion and a thread portion; and
a tulip assembly comprising an upper portion and a lower portion, wherein the upper portion of the tulip assembly is configured to receive and retain a rod and a locking cap, and wherein the lower portion of the tulip assembly is configured to receive and retain the head portion of the threaded screw;
wherein the lower portion of the tulip assembly comprises a separate locking collar disposed concentrically about the lower portion of the tulip assembly and a plurality of spring members, wherein the plurality of spring members have a continuously increasing collective external diameter that is smaller adjacent an upper portion of the plurality of spring members and larger adjacent a lower portion of the plurality of spring members, and wherein, when the locking collar is translated from a first position about the smaller external diameter upper portion of the plurality of spring members to a second position about the larger external diameter lower portion of the plurality of spring members, the plurality of spring members transition from an expanded configuration in which the tulip assembly is allowed to pivot with respect to the threaded screw to a compressed configuration in which the tulip assembly is prevented from pivoting with respect to the threaded screw; and
wherein an internal diameter of the locking collar decreases from an end proximate the upper portion of the tulip assembly to an end proximate the lower portion of the tulip assembly.

2. The bone screw of claim 1, wherein the head portion of the threaded screw is substantially spherical in shape.

3. The bone screw of claim 1, wherein the locking cap is externally threaded and is configured to engage threads manufactured into an interior portion of the tulip assembly.

4. The bone screw of claim 1, wherein the plurality of spring members define a substantially spherical internal space.

5. The bone screw of claim 1, wherein the locking collar is configured to be translated from the first position to the second position using a tool.

6. The bone screw of claim 1, wherein the locking collar is translated from the first position to the second position via deflection of the rod directly into the wider internal diameter end of the locking collar external to the tulip assembly by insertion and rotation of the locking cap into the tulip assembly, wherein the rod simultaneously directly contacts both the locking cap and the wider internal diameter end of the locking collar when the locking cap is inserted and rotated into the tulip assembly.

7. The bone screw of claim 1, wherein the plurality of spring members are disposed concentrically about the head portion of the threaded screw.

* * * * *

UNITED STATES PATENT AND TRADEMARK OFFICE
CERTIFICATE OF CORRECTION

| | |
|---|---|
| PATENT NO. | : 9,895,171 B2 |
| APPLICATION NO. | : 14/812160 |
| DATED | : February 20, 2018 |
| INVENTOR(S) | : Webb et al. |

It is certified that error appears in the above-identified patent and that said Letters Patent is hereby corrected as shown below:

On the Title Page

Item (12) "Webb" is corrected to --Webb et al.--.

Item (72) Inventor is corrected to read:
--Scott A. Webb, Clearwater, FL (US);
Boyle Cheng, Greeley, CO (US)--.

Signed and Sealed this
Fourteenth Day of June, 2022

Katherine Kelly Vidal
*Director of the United States Patent and Trademark Office*